(12) United States Patent
Lee et al.

(10) Patent No.: US 8,552,163 B2
(45) Date of Patent: Oct. 8, 2013

(54) LIVER-TARGETING AGENTS AND THEIR SYNTHESIS

(75) Inventors: Reiko Takasaka Lee, Baltimore, MD (US); Yuan-Chuan Lee, Baltimore, MD (US); Mei-Hui Wang, Taoyuan County (TW); Wuu-Jyh Lin, Taoyuan County (TW)

(73) Assignees: Johns Hopkins University, Baltimore, MD (US); Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 196 days.

(21) Appl. No.: 12/891,004

(22) Filed: Sep. 27, 2010

(65) Prior Publication Data

US 2011/0077386 A1 Mar. 31, 2011

Related U.S. Application Data (60) Provisional application No. 61/245,711, filed on Sep. 25, 2009.

(51) Int. Cl.
*C07H 17/02* (2006.01)
*C07C 229/00* (2006.01)

(52) U.S. Cl.
USPC .......................................... 536/17.9; 562/572

(58) Field of Classification Search
USPC ......................................... 536/17.9; 562/572
See application file for complete search history.

(56) References Cited

PUBLICATIONS

YC Lee, RR Townsend, MR Hardy, J Lonngren, J Arnarp, M Haralsddon and H Lonn "Binding of Synthetic Oligosaccharides to the Hepatic Gal/GalNAc Lectin" JBC 258, pp. 199-202, 1983.
SK Ha-Kawa and Y Tanaka "A Quantitative Model of Technetium-99m-DTPA-Galactosyl-HAS for the Assessment of Hepatic Blood Flow and Hepatic Binding Receptor" J Nucl Med 1991;32:2233-2240.
C Plank, K Zatloukal, M Cotton, K Mechtler and E Wagner "Gene Transfer into Hepatocytes Using Asialoglycoprotein Receptor Mediated Endocytosis of DNA Complexed with ab Artificial Tetra-Antennary Galactose Ligand" Bioconjugate Chem 3:533-539, 1992.
JR Merwin, GS Noell, WL Thomas, HC Chiou, ME DeRome, TD McKee, GL Spitalny and MA Findeis "Targeted Delivery of DNA Using YEE (GalNAcAH)3, a Synthetic Glycipeptide Ligand for the Asialoglycoprotein Receptor" Bioconjugate Chem 5:612-620, 1994.
JJ Hangeland, JT Levis, YC Lee and POP Ts'o "Cell-Type Specific and Ligand Specific Enhancement of Cellular Uptake of Oligodeoxynucleoside Methylphophonates Covalently Linked with a Neoglycopeptide, YEE(ah-GalNAc)3" Bioconjugate Chem 6:695-701,1995.
JJ Hangeland, JE Flesher, SF Deamond, YC Lee, POP Ts'o and JJ Frost "Tissue Distribution and Metabolism of the P-32 Labeled Oligodeoxynucleoside Methylphosphonate-Neoglycopeptide Conjugate, [YEE(ah-GalNAc)3]-SMCC-AET-pUmpT7 in the mouse" Antisense and Nucleic Acid Drug Development 7:141-149, 1997.
H Toyama, K Suzuki, A Naito, M Kuroda, K Kikukawa, Y Komori, A Hasumi, K Matsumura, T Fujiwara, K ito, K Ejiri, K Senda, A Takeuchi and S Koga "Evaluation of asialoglycoprotein receptor imaging agent as a marker of hepatic ischemia-reperfusion injury and recovery." Annals of Nuclear medicine 13(3):155-160, 1999.
AH Kwon, T Inoue, and SK Ha-Kawa "Characterization of the Asialoglycoprotein Receptor Under Hypoxic Conditions in Primary Cultured Rat Hepatocytes" J Nucl Med 46:321-325, 2005.
RT Lee and YC Lee "Facile Synthesis of a High-Affinity Ligand for mammalian Hepatic Lectin Containing Three Terminal N-Acetylgalactosamine Residues" Bioconjugate Chem 8:762-765, 1997.

*Primary Examiner* — Eric S Olson
*Assistant Examiner* — Zhengfu Wang
(74) *Attorney, Agent, or Firm* — WPAT, PC; Justin King

(57) ABSTRACT

This invention provides novel liver targeting agents and their synthetic methods. A liver targeting agent, with a lysine based nitrilotriacetic acid structure as backbone which acquires multivalency with saccharide groups, to bind with a galactosamine chain or lactose chain is disclosed. In particular, only one amino acid L-lysine is involved to provide trivalency. All carboxyl groups in $N^\epsilon$-benzyloxycarbonyl-$N^\alpha$-dicarboxymethyl-L-lysine can be conjugated with three glycosides of ahGalNAc or ahLac in one step. This invention also provides a hexa-lactoside. In particular, the TFA-AHA-Asp was used to conjugate 2 molecules of $NTA(ahLac)_3$. This invention also provides a method for adding a spacer between NTA and DTPA. The extended hepatocyte-specific glyco-ligand has higher $^{111}$In-radiolabelling yield than those non-extended.

5 Claims, 11 Drawing Sheets

I: R=CH$_2$CONH(CH2)$_6$O-GalNAc
II: R=(CH2)$_6$O-Lactose

III: R=(CH$_2$)$_6$O-Lactose

LIVER-TARGETING AGENTS AND THEIR SYNTHESIS

CROSS-REFERENCE TO RELATED APPLICATIONS

This application claims the benefit of U.S. Provisional Application No. 61/245,711, filed on Sep. 25, 2009, which is herein incorporated by reference in its entirety.

BACKGROUND OF THE INVENTION

1. Field of the Invention

The present invention relates to novel hepatocyte-specific tri-valent ligands based on nitrilotriacetic acid (NTA) having three N-acetylgalactosamine (GalNAc) or three or six lactose (Lac) moieties attached to the NTA structure.

2. Related Art

Asialoglycoprotein receptor (ASGPR) of the liver is known to specifically bind to glycopeptides or glycoproteins having Gal or GalNAc on an end. When liver lesion occurs, the number of ASGPR will decrease. Therefore, it is desirable to develop high-affinity ligands for ASGPR with multiple Gal or GalNAc terminal residues useful for imaging of ASGPR activities.

This type of liver receptor activity imaging agents has the potential of quantifying the liver storage function and also has the ability to determine the residual liver function in a patient to allow clinicians to determine whether a liver transplantation is necessary or not. In Taiwan, there are 3,000,000 patients with hepatitis B, 500,000 patients with hepatitis C, and numerous patients with drug-induced hepatitis, all of whom are at high risk of liver failure and need regular assessment of liver storage function.

Presently, the peptides or proteins to be acquired multivalency with saccharide groups known in the art include albumin, tyrosine-glutamyl-glutamic acid (YEE), tyro sine-aspartyl-aspartic acid (YDD), and tyro sine-glutamyl-glutamyl-glutamic acid (YEEE).

Tc-99m-Galactosyl-Serum-Albumin (Tc-99m GSA) is known as a liver receptor imaging agent and has been used clinically in Japan. But, GSA is a carbohydrate-modified protein based on human serum albumin, which is a biological product having a very high molecular weight of about 67 kD. In such a product, it is difficult to know the exact position of modification and the precise number of the sugar attachment, not to mention DTPA (diethylene triamine pentaacetate) further attaches to GSA for labeling. In contrast, YEE, YDD, and YEEE are based on peptides having a molecular weight of only about 1-2 kD, and the exact structures, including the DTPA, are known. Thus the quality control procedures are significantly simplified compared to those procedures used with GSA.

YEE(ahGalNAc)$_3$ and YDD(ahGalNAc)$_3$ were first reported by Lee (1983), but their poor solubility limited their development. YEEE(ahGalNAc)$_3$ is an improved version reported by Chen (TW1240002, 2000). However, the overall yield is still unsatisfactory, the cost of GalNAc is considerably high, and it is not commercially available.

In 1983, Lee et al. reported that the binding affinity of divalent GalNAc-containing peptide by rat hepatocytes is 1000 times stronger than that of its monovalent GalNAc counterpart and the binding affinity between trivalent GalNAc ligand with hepatocytes receptor is $10^6$ times greater than that of monovalent GalNAc ligand peptide with a single chain.

It should be noted that in YEE, YDD, and YEEE derivatives, a branching scaffold is provided by peptides rather than sugars as in natural glycoproteins, for example, γ-glutamyl-glutamic acid (abbreviated as "EE"), and β-aspartyl-aspartic acid (abbreviated as "DD"). Both EE and DD have three COOH functional groups being exposed and can thus be joined with three w-amino glycosides of GalNAc. However, the disadvantage of these compounds and tedious chemical synthetic process impeded their further development.

Therefore, it is desirable to develop a new type of high affinity reagents for hepatocytes (targeting ASGPR) which are convenient to synthesize and processing adequate solubility.

SUMMARY OF THE INVENTION

In certain aspects of the current invention, only one amino acid, L-lysine is used to provide trivalency, thus greatly abbreviating the synthetic procedure. N$^\epsilon$-protected lysine can be carboxymethylated with glycolic acid (CHOCOOH) under reductive conditions or with bromoacetic acid to obtain a "nitrilo-triacetic acid (NTA)" group. All carboxyl groups in the NTA structure can be conjugated with three glycosides of GalNAc or Lac in one step. In addition, Nα-dicarboxymethyl L-Lysine is commercially available, which can save some time and expense in the chemical synthesis, if such a path is to be sought for mass production of the multi-valent liver targeting agents. In the present application, CBZ-NTA was designed to link ahGalNAc or ahLac.

In particular aspects, a detailed one-pot preparation of raw materials and products is described herein.

In other aspects, the present invention relates to novel hepatocyte-specific glyco-ligands comprising lysine-based hexa-valent lactose or tri-valent galactosamine ligands.

In some aspects, the present invention is amenable to mass-production.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Having thus described the presently disclosed subject matter in general terms, reference will now be made to the accompanying Drawings, which are not necessarily drawn to scale, and wherein:

DETAILED DESCRIPTION OF THE INVENTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

I Design of Novel Liver Targeting Drug

Figure 1:
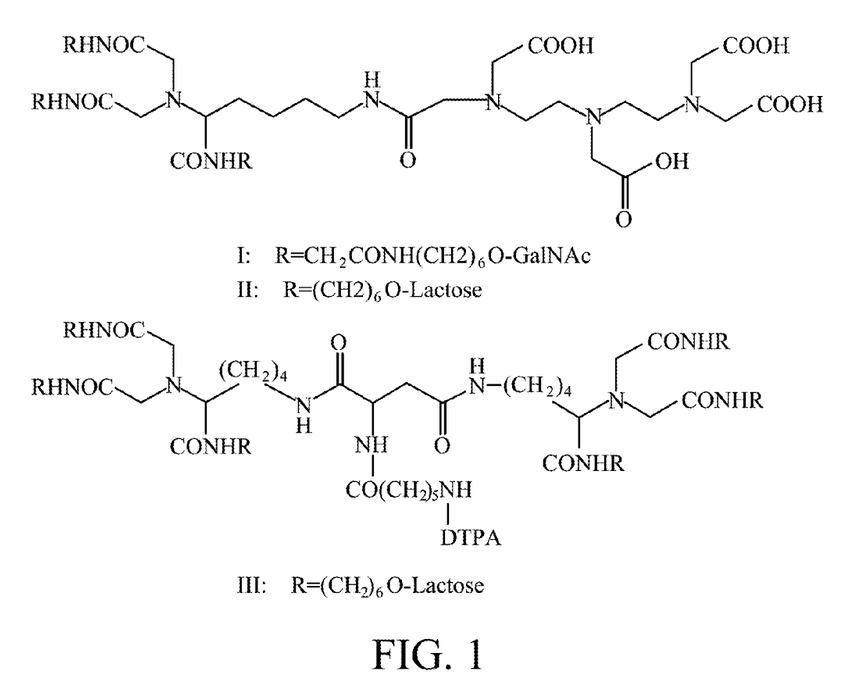
FIG. 1 is a structural representation of the presently disclosed liver targeting drug.

In the present invention, $N^\epsilon$-benzyloxycarbonyl-$N^\alpha$-dicarboxylmethyl-L-lysine (Z-DCM-Lys) is used as a new basic structure to connect with 6-aminohexyl β-GalNAc (ah-GalNAc), glycyl-aminohexyl β-GalNAc (GahGalNAc), or aminohexyl Lac (ah-Lac), so as to form a three-chain glycopeptide. As the binding affinity of the trivalent Lac ligand to the ASGPR is not as strong as that of the trivalent GalNAc ligand, the trivalent Lac ligand is cojoined via an aspartic acid or a glutamic acid derivative from a hexa-valent Lac ligand. For example, two molecules of trivalent glycosides of $N^\epsilon$—Z—$N^\alpha$-DCM-Lys-(ahLac)$_3$ and 6-aminohexanoyl aspartic acid (AHA-Asp) form AHA-Asp[DCM-Lys(ahLac)$_3$]$_2$ (hereafter simply referred to as hexa-Lactoside). The free amino end of the hexa-Lactoside can be modified with DTPA anhydride in a sodium carbonate solution to form a DTPA derivative of AHA-Asp[DCM-Lys(ahLac)$_3$]$_2$, the structure of which is as shown in FIG. 1.

II Analysis of Binding Strength of Saccharide Chain Peptide and Murine Hepatocyte With Eu-asialo-orosomucoid (Eu-ASOR) as a reference material, the binding affinity of the multivalent glyco-ligands (DCM-Lys(ah-GalNAc)$_3$, DCM-Lys(GahGalNAc)$_3$, DCM-Lys(ahLac)$_3$, AHA-Asp[DCM-Lys(ahLac)$_3$]$_2$) and murine hepatocyte can be determined by competitive assay to obtain IC$_{50}$ (concentration of 50% inhibition), and the lower the IC$_{50}$ is, the higher the binding affinity. The murine hepatocyte (Lonza Biotechnology Company, Walkersville, Md.) is plated in a 24-well plate in advance, and the reaction occurs in each well, into which (i) Eu-ASOR 10 nM (ii) hepatocyte basic medium with 5 mM calcium chloride, and (iii) five different concentrations of multivalent ligands of 1 μM-0.8 nM are added. After culturing with shaking for 1 hr in the cold, the unbound ligands are removed by washing with the hepatocyte basic medium containing calcium chloride. Time-resolved fluorometry (TRF) is performed, using an enhancement solution (15 μM β-naphthoyl trifluoroacetone, 50 μM tri-n-octyl-phosphine oxide, 0.1% triton X-100 in 0.1 M acetic acid, titrated with potassium hydrogen phthalate to pH 3.2). The enhancement solution reacts with Eu$^{3+}$ to form an Eu chelate, which can emit at 615 nm when excited at 340 nm. With the logarithm of the concentration of saccharide chain peptide as X axis, the emitted fluorescence value as Y axis, the fluorescence value without adding glycopeptide being set as 100%, the IC$_{50}$ values of each ligand can be calculated accordingly. From these data, it is clear that the binding of AHA-Asp [DCM-Lys(ahLac)$_3$]$_2$ and ASGPR can reach the same binding strength as that of YEE or YDD, but the binding of DCM-Lys(GahGalNAc)$_3$ and ASGPR is 10 times higher than that of YEE or YDD, as shown in Table 1.

TABLE 1

Comparison of binding strength of various saccharide chains and murine hepatocyte

| Compounds | IC50(nM) |
|---|---|
| YEE(ahGalNAc)$_3$ | 10 nM |
| YDD(GahGalNAc)$_3$ | 10 nM |
| DCM-Lys(ahGalNAc)$_3$ | 10 nM |
| DCM-Lys(GahGalNAc)$_3$ | 1 nM |
| AHA-Asp[DCM-Lys(ahLac)$_3$]$_2$ | 10 nM |

Figure 2:
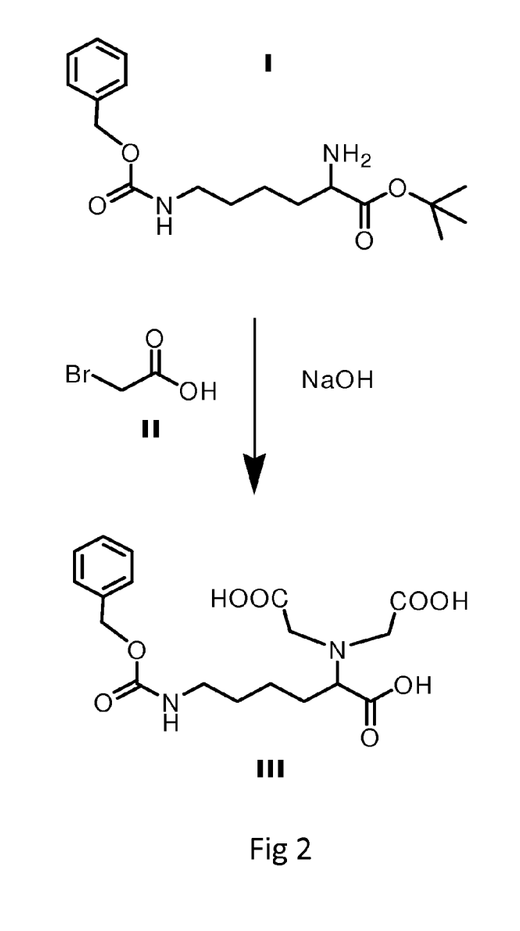
FIG. 2 is scheme of a one-pot preparation of N$^\epsilon$-benzyloxycarbonyl-N$^\alpha$-Dicarboxymethyl-L-Lysine.

III One-Pot Preparation of $N^\epsilon$-benzyloxycarbonyl-$N^\alpha$-Dicarboxymethyl-L-Lysine The scheme is shown in FIG. 2 and the method follows Biomaterials (09) 30:836-842, with some minor modification. $N^\epsilon$-benzyloxycarbonyl-L-lysine(OtBu) (I), 2 g (15.1 mmol), was dissolved in 25 mL of 1.5 M NaOH, to which was added dropwise a solution of bromoacetic acid (II), 4.15 g (30.2 mmol) in 15 mL of 1.5 M NaOH. The mixture was allowed to stand 16 h at room temperature and then heated at 55° for 3 h. The near neutral solution was cooled to room temperature and mixed with 4 M HCl (12 mL), whereupon copious white precipitate appears. The precipitate was filtered and washed with cold water, and dried in a desiccator containing NaOH pellets overnight. The dry crystals (2.5 g, 40% yield) showed correct structure (III) by NMR.

IV One-Pot Synthesis of 6-(trifluoroacetylamido)hexanol

Figure 3:
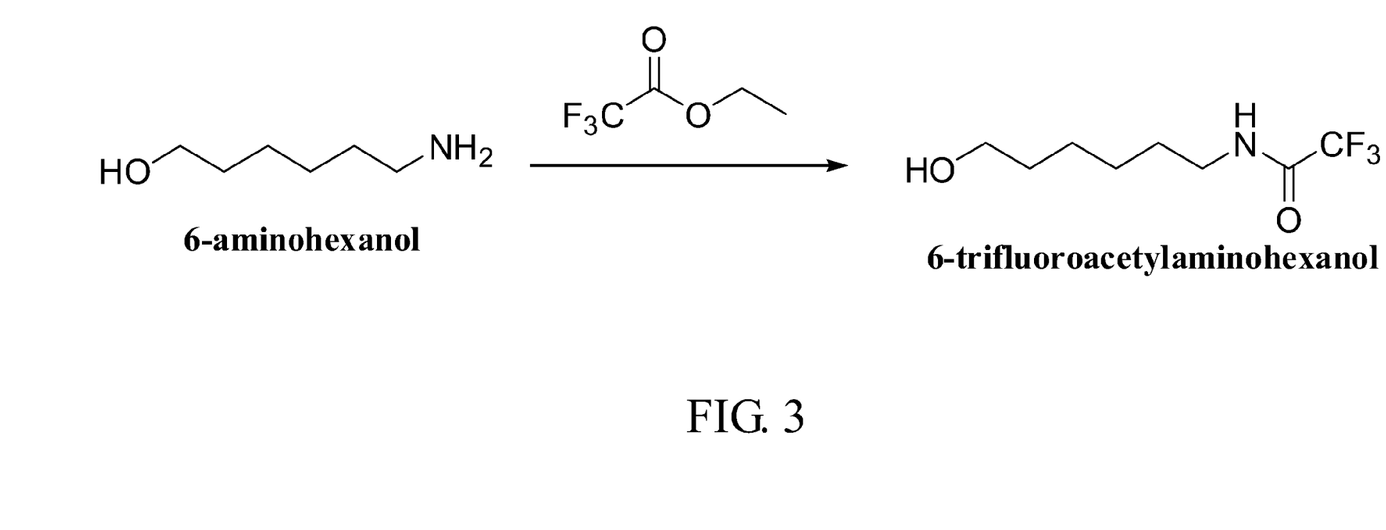
FIG. 3 is scheme of a one-pot synthesis of 6-(trifluoroacetylamido)hexanol.

The scheme is shown in FIG. 3. 6-aminohexanol (1 eq) and ethyl trifluoroacetate (99%, 1 eq) is added at room temperature with stirring for 5 hr. The resulting solution is added to cold water and continuously stirred for 14 hr in the cold. White precipitate formed is harvested by filtration (yield 42%). The structure of 6-(trifluoroactamido)hexanol (TFA-ah) was confirmed by $^1$H-NMR.

V Synthesis of ahLac

Figure 4:
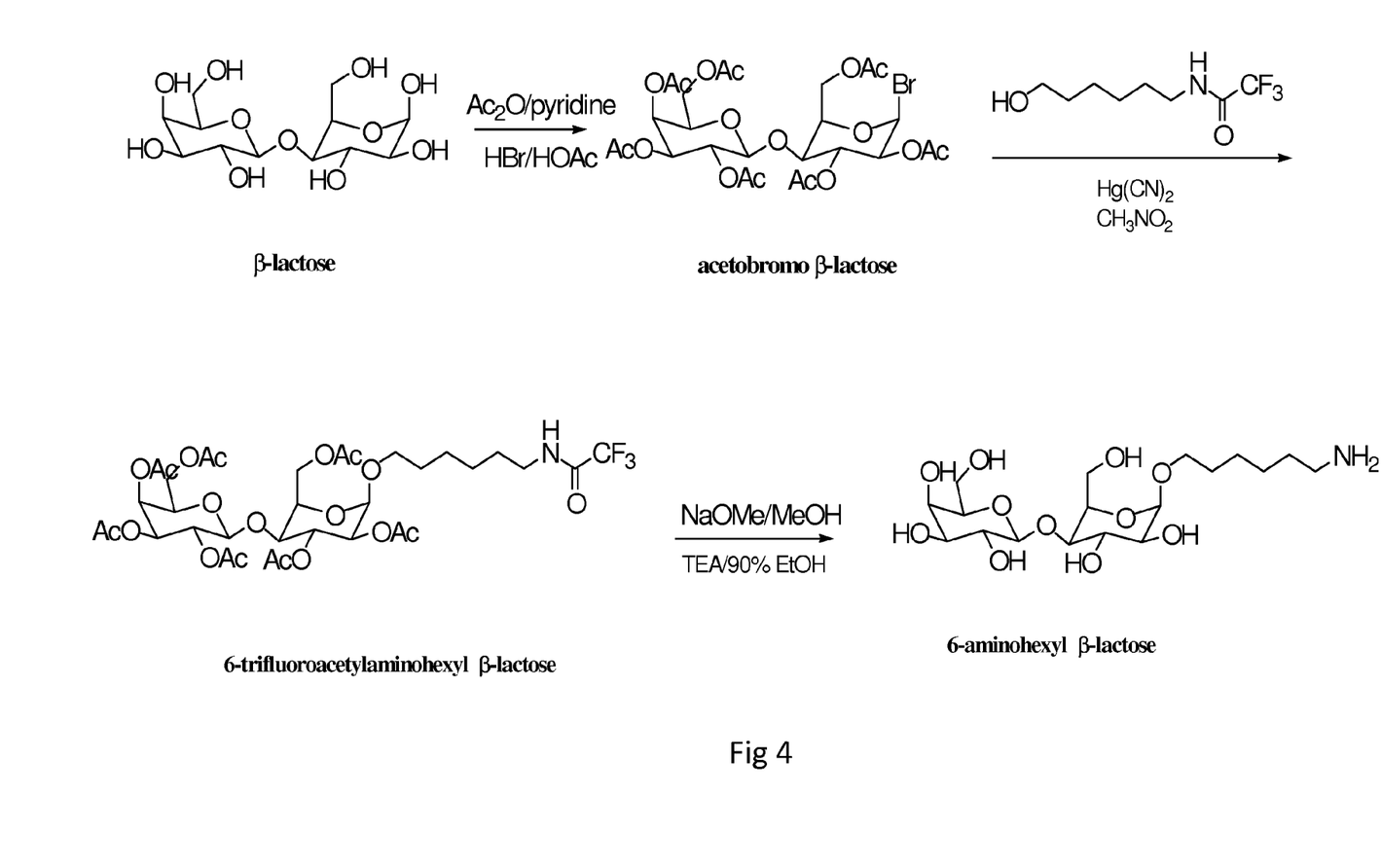
FIG. 4 is scheme of the synthesis of ahLac.

The scheme is shown in FIG. 4.

The β-acetobromo-β-lactose was prepared in one step according to the method of Kartha et al (Journal of Carbohydrate Chemistry, 9, 777-781, 1990). The β-lactose is treated with acetic anhydride and HBr/HOAC in one flask. After the acetobromo sugar is formed, extra reagents are flash evaporated. Addition of ether provided beautiful crystal.

TFA-ah-Lac was synthesized according to the method of Weigel et al (Carbohydr Res 70, 83-91, 1979). TFA-ah was reacted with β-acetobromo β-lactose in 1:1 (v/v) benzene-nitromethane, with mercuric cyanide as the catalyst.

De-O-acetylation was carried out in dry methanolic solution containing 10 mM sodium methoxide for 2 hr at room temperature. The reaction mixture was neutralized with Dowex 50 (H$^+$ form), filtered and the filtrate was evaporated.

De-N-trifluoroacetylation was done in aqueous solution containing 10% ethanol and 10% triethylamine (TEA) for overnight at room temperature. The mixture was evaporated to dryness, and the residue was dried in a vacuum dessicator over NaOH pellets and concentrated sulfuric acid. In order to remove the counterion of the amino group, the residue was dissolved in 50% ethanol and treated with Dowex 1 (OH⁻ form) until supernatant solution is alkaline, and then filtered and the filtrate is evaporated.

VI Synthesis of ahGalNAc

Figure 5:
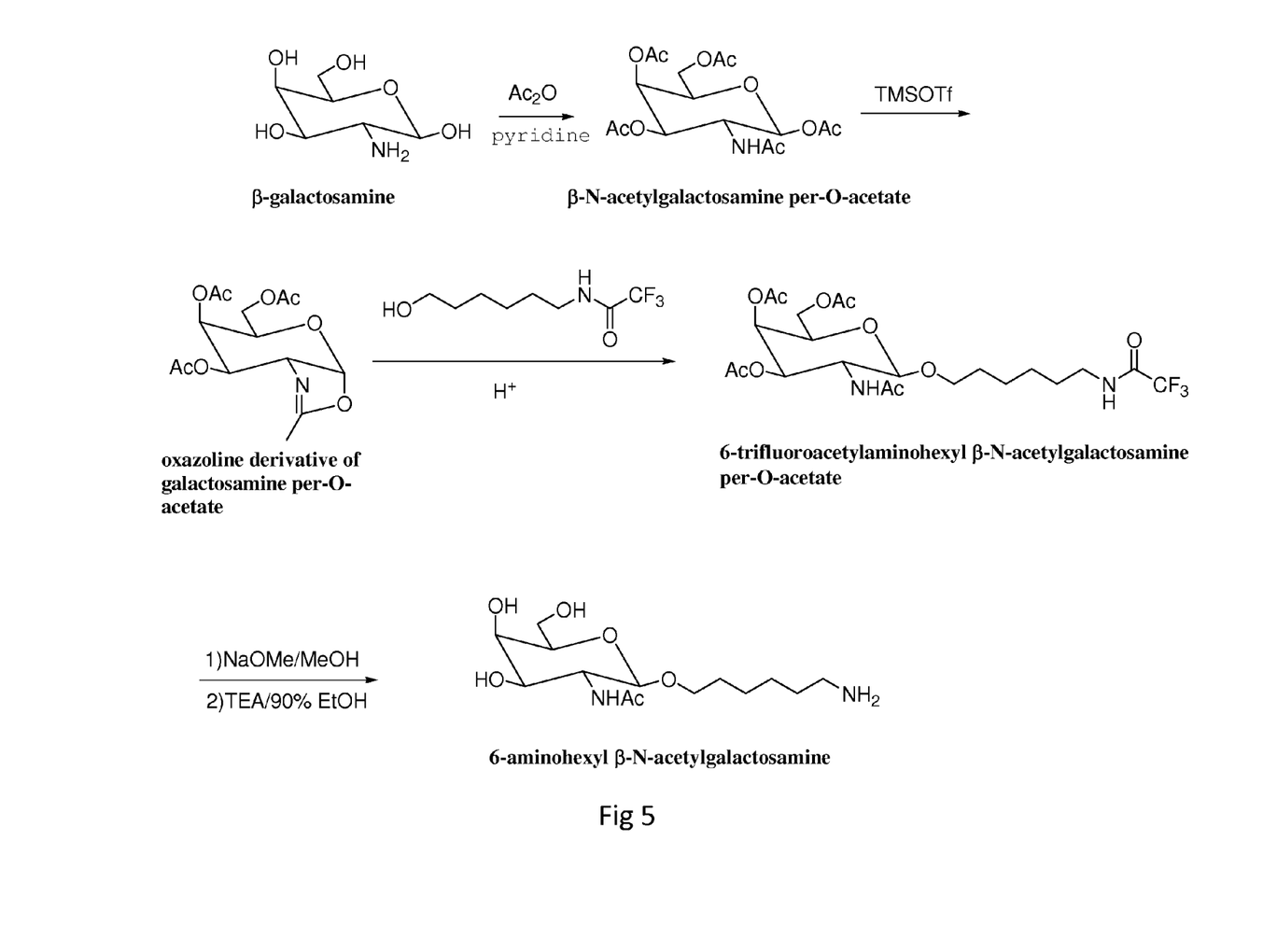
FIG. 5 is scheme of the synthesis of ahGalNAc.

The scheme is shown in FIG. 5. Galactosamine hydrochloride is treated with acetic anhydride and pyridine at room temperature for 16 hr. The white precipitate is the per-o-acetyl GalNAc with a yield 76.7%. Formation of oxazoline derivative from per-o-acetyl GalNAc and subsequent glycoside formation were done according to the published method of Wu and Gao (Bioconjug Chem 17, 1537-44, 2006) with minor modification. To a solution of per-o-acetyl GalNAc in dichloroethane was added trimethylsilyl trifluoromethane sulfonate (TMSOTf) and the mixture was heated at 50° C. for 10 hr. Triethylamine was added to quench the acid. The reaction mixture was evaporated, the residue was dissolved in chloroform, and the chloroform solution was washed with cold saturated sodium bicarbonate (twice) and with 1M NaCl (once). The chloroform layer was dried with anhydrous sodium sulfate, filtered and evaporated. The dark red syrup was oxazoline derivative with yield 99%. This compound is unstable and it is better to proceed to the next step immediately. The oxazoline derivative obtained above and TFA-ah were dissolved in methylene chloride. Molecular sieve (4 Å) was added and the mixture was flushed with nitrogen gas, and stirred at room temperature for 1 hr. Concentrated sulfuric acid was then added, and the mixture was stirred overnight. The reaction mixture was filtered through a pad of Celite on a sintered-glass filter. The filtrate was diluted with methylene chloride and the solution was washed with cold saturated sodium bicarbonate (twice) and 1M NaCl (once). The residue was dissolved in 95% ethanol and fractionated on a Sephadex LH20 column using 95% ethanol as eluant. Only the product TFA-ah-GalNAc(OAc)₃ were combined and evaporated.

De-O-acetylation was carried out in dry methanolic solution containing 10 mM sodium methoxide for 2 hr at room temperature. The reaction mixture was neutralized with Dowex 50 (H⁺ form), filtered and the filtrate was evaporated. De-N-trifluoroacetylation was done in aqueous solution containing 10% ethanol and 10% triethylamine (TEA) for overnight at room temperature. The mixture was evaporated to dryness, and the residue was dried in a vacuum dessicator over NaOH pellets and concentrated sulfuric acid. In order to remove the counterion of the amino group, the residue was dissolved in 50% ethanol and treated with Dowex 1 (OH⁻ form) untilsupernatant solution is alkaline, and then filtered and the filtrate is evaporated.

VII Synthesis of NTA-(ahLac)₃

Figure 6:
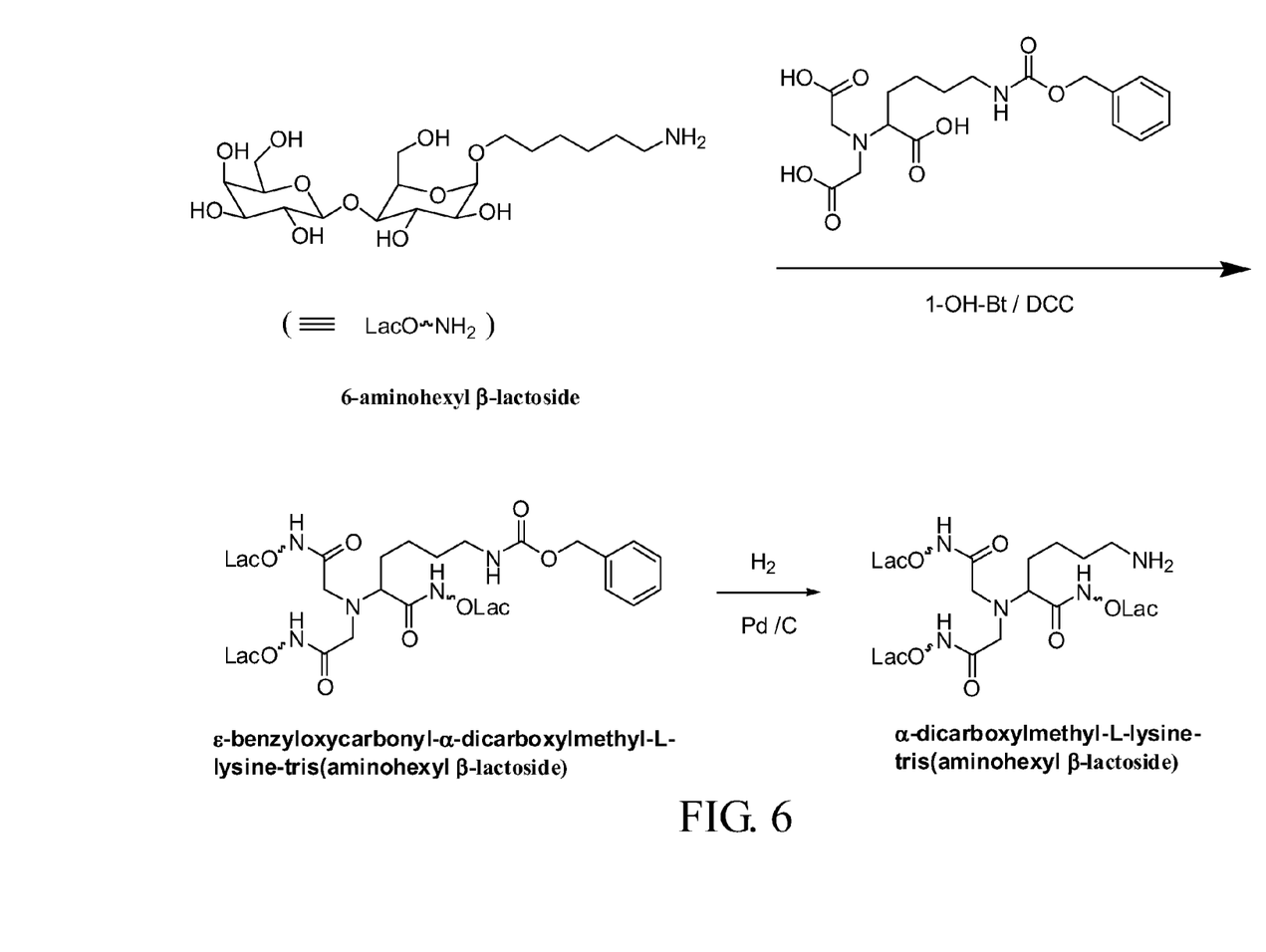
FIG. 6 is scheme of the synthesis of NTA-(ahLac)$_3$.

The scheme is shown in FIG. 6. 1.3 mmol 6-ah-β-lactoside was conjugated with 0.34 mmol Cbz-NTA with the aid of DCC/1-OH-Bt in DMSO. The reaction mixture was fractionated on Sephadex G-15 in 0.1M acetic acid. Fractions containing the trivalent product were combined and evaporated. Solid product was obtained by dissolving the residue in water-ethanol mixture and precipitating the product by adding ether.

Removal of benzyloxycarbonyl (Z) group was by hydrogenation in a Brown hydrogenator at atmospheric pressure, using either 60% acetic acid or 95% ethanol, and 10% Pd on carbon (about 10% of the weight of Z-containing compound) as catalyst. After the overnight treatment, the removal of Cbz-group was complete, as judged by TLC in ethyl acetate-acetic acid-water (2:1:1, v/v). After filtration, the filtrate was evaporated. The resulting compound is NTA-(ahLac)₃.

VIII One-pot preparation of NTA-(ahGalNAc)₃

Figure 7:
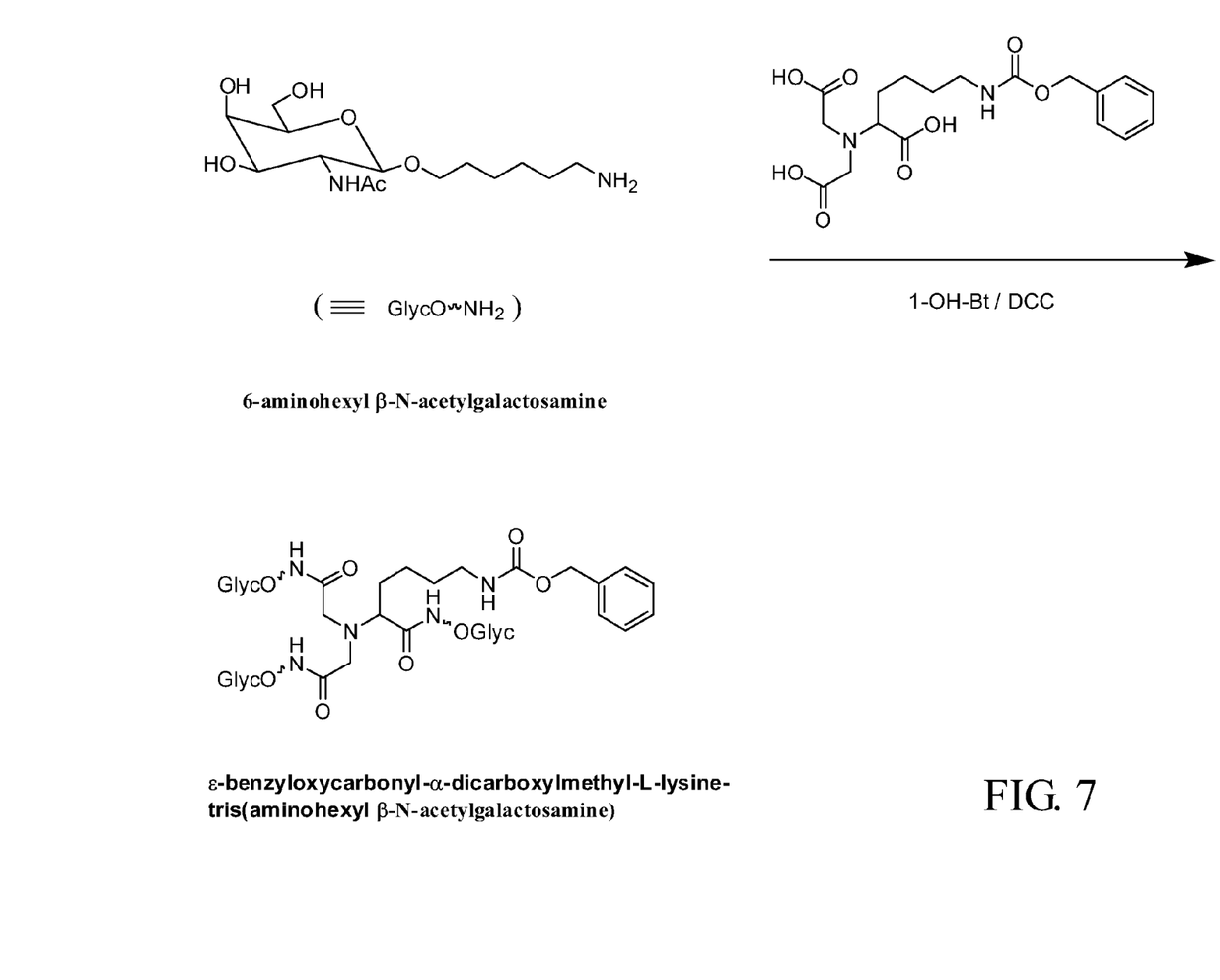
FIG. 7 is scheme of a one-pot preparation of NTA-(ahGalNAc)$_3$.

The scheme is in FIG. 7. 0.45 mmol 6-ah-GalNAc was conjugated with 0.1 mmol Cbz-NTA with the aid of DCC/1-OH-Bt in dry DMF. The mixture was stirred at room temperature overnight. DCU formed was filtered and filtrate was evaporated. Filtrate was fractionated on the Sephadex G-15 column in 0.1M acetic acid. Fractions containing the trivalent product were combined and evaporated.

Removal of benzyloxycarbonyl (Z) group was by hydrogenation in a Brown hydrogenator at atmospheric pressure, using either 60% acetic acid or 95% ethanol, and 10% Pd on carbon (about 10% of the weight of Z-containing compound) as catalyst. After the reaction, the mixture was filtered and the filtrate was evaporated.

IX One-Pot Preparation of TFA-AHA-Asp

Figure 8:
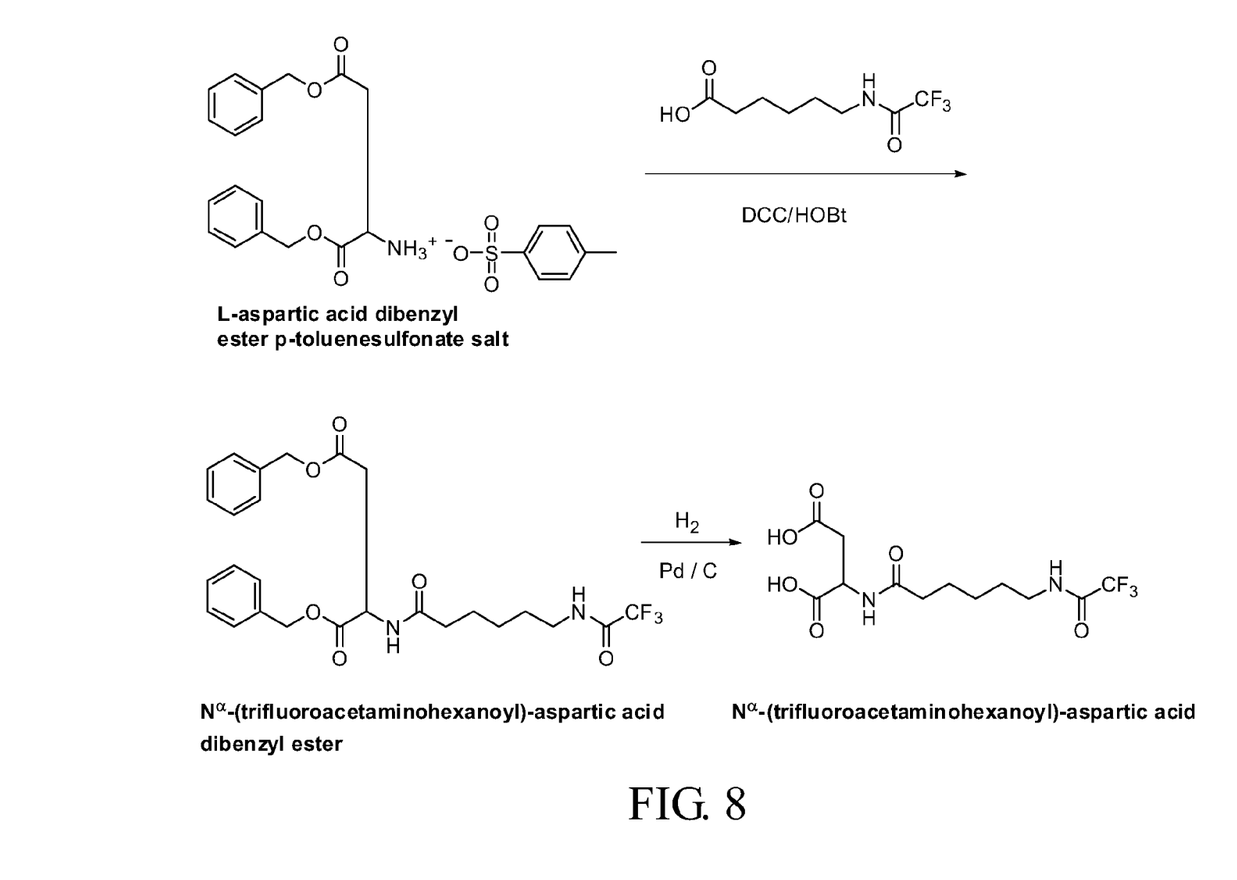
FIG. 8 is scheme of a one-pot preparation of TFA-AHA-Asp.

The scheme is shown in FIG. 8. L-aspartic acid dibenzyl ester p-toluenesulfonate salt was conjugated with TFA with the aid of DCC/1-OH-Bt in dry DMF. The mixture was stirred at room temperature overnight. DCU formed was filtered and filtrate was evaporated. Filtrate was fractionated on the Sephadex G-15 column in 0.1M acetic acid.

X One-Pot Preparation of Hexa-Valent Lactoside

Figure 9:
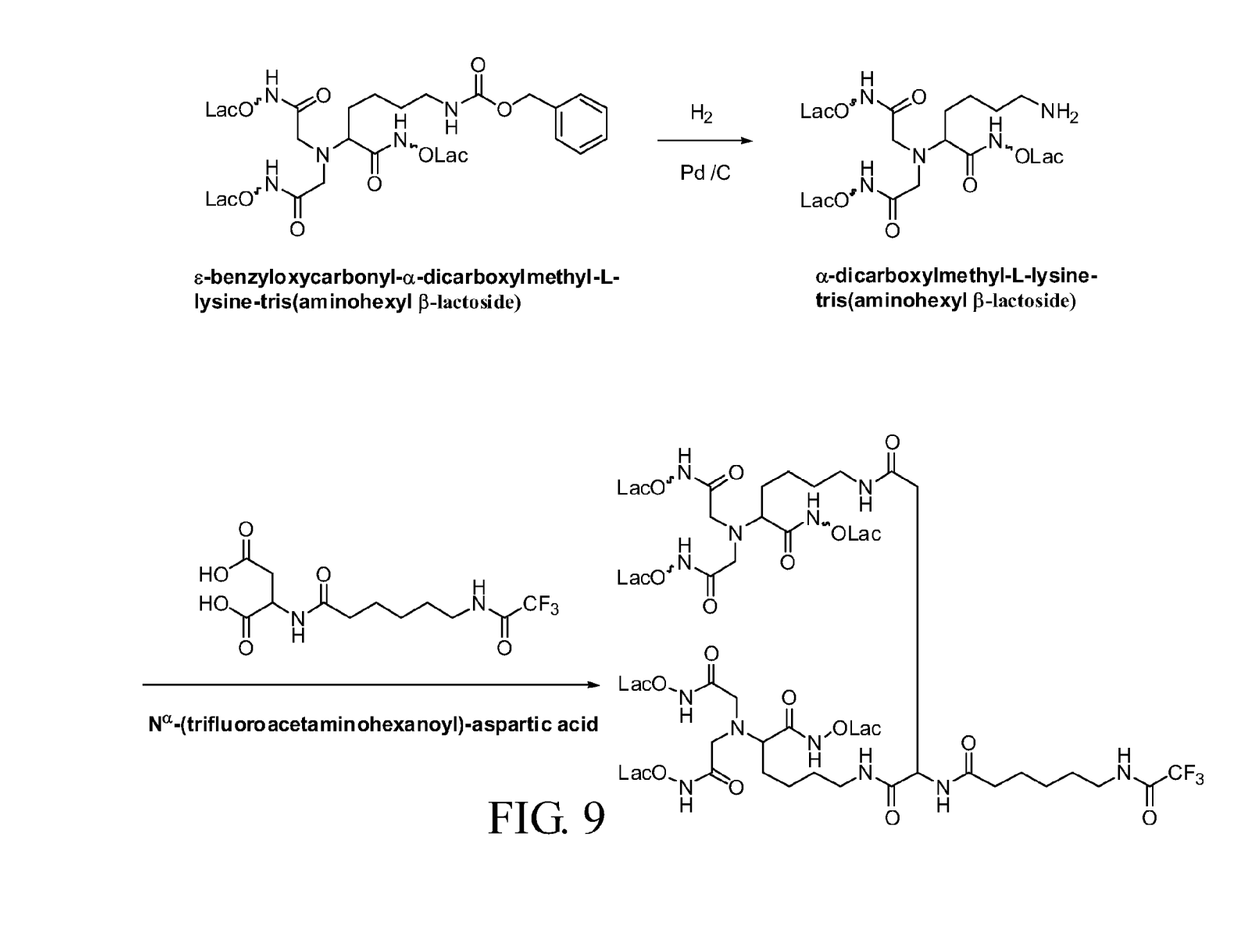
FIG. 9 is scheme of a one-pot preparation of hexa-valent lactoside.

The scheme is shown in FIG. 9. The process for preparing hexa-valent lactoside involves: 1) conjugation of NTA-(ahLac)₃ with TFA-AHA-Asp, [CF₃CONH(CH₂)₅CONHCH(CH₂COOH)COOH], in DMSO with the help of DCC/1-OH-Bt. The mixture was stirred at room temperature overnight. DCU formed was filtered and filtrate was evaporated. Filtrate was fractionated on the Sephadex G-15 column in 0.1M acetic acid. Fractions containing the hexa-valent lactoside were combined and evaporated; 2) De-N-trifluoroacetylation was done in aqueous solution containing 10% ethanol and 10% triethylamine (TEA) for overnight at room temperature. The mixture was evaporated to dryness, and the residue was dried in a vacuum dessicator over NaOH pellets and concentrated sulfuric acid.

XI Trivalent GalNAc Liver-Targeting Ligand with a Longer Arm

Figure 10A:
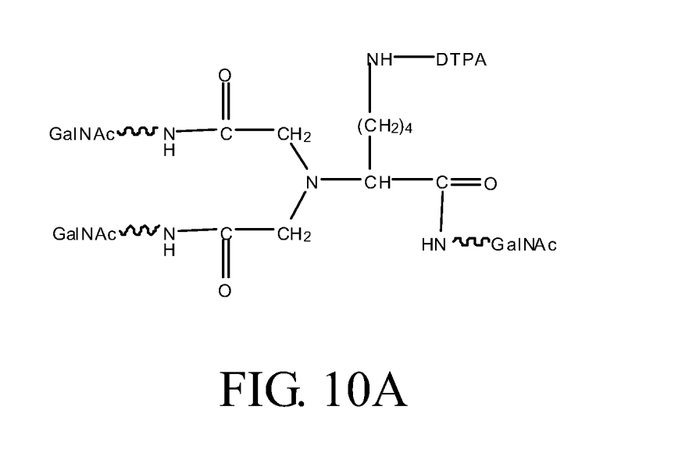
FIG. 10A is scheme of a presently disclosed trivalent GalNAc liver-targeting ligand.

The scheme is shown in FIG. 10.

In a radiolabelling experience, DTPA-labeled tri-valent GalNAc ligand [ε-DTPA-α-DCM-Lys(G-ahGalNAc)₃] (FIG. 10A), hereinafter referred to as "tri(GalNAc)", did not complex well with 111-Indium, even with a very high ratio of the Glyco-ligand to indium ratio. In comparison, the HexaLac (FIG. 10C) was readily labeled with indium. Without wishing to be bound to any one particular theory, this indicated that perhaps the DTPA residue in tri(GalNAc) is too close to the main body of the tri-valent GalNAc structure, so that indium could not access the chelating agent easily.

Figure 10B:
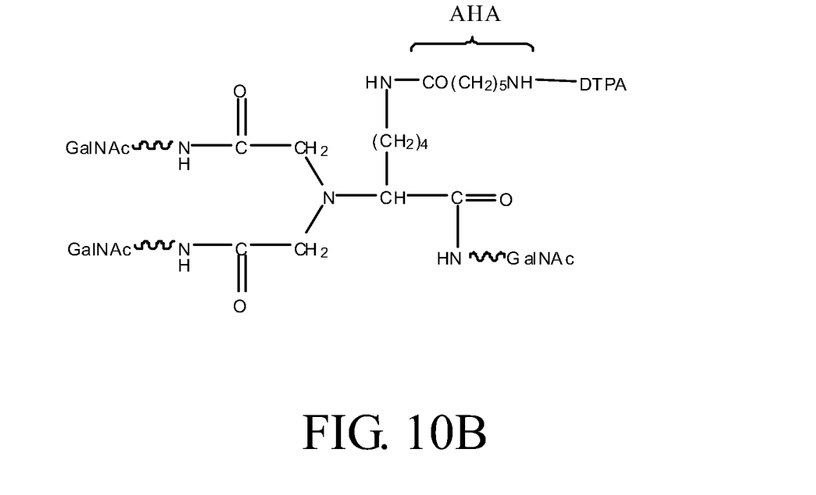
FIG. 10B is scheme of a presently disclosed trivalent GalNAc liver-targeting ligand with a longer arm.
Figure 10C:
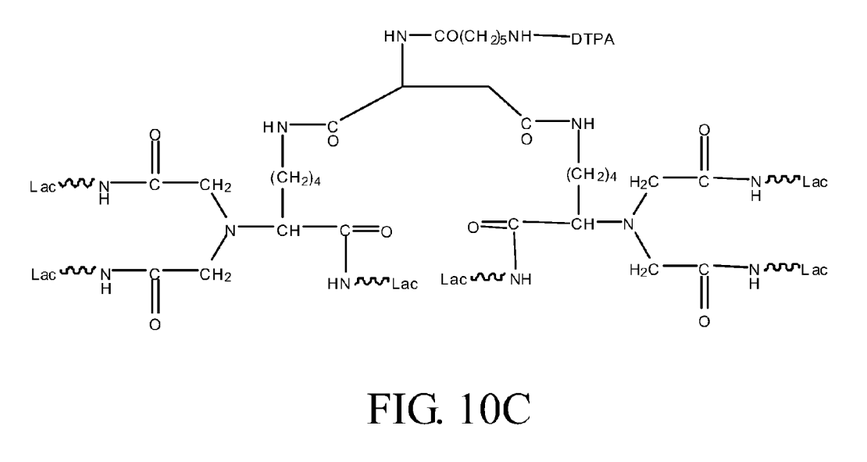
FIG. 10C is scheme of a presently disclosed hexavalent Lac liver-targeting ligand.

Therefore, the ε-amino group of α-DCM-Lys(G-ah-GalNAc)₃ was extended with a 6-carbon arm, as depicted in FIG. 10B. Starting from the existing stock of ε-Z-α-DCM-Lys(G-ah-GalNAc)₃ (FIG. 10A), this process involved: 1) removal of benzyloxycarbonyl (Cbz) protective group; 2) conjugation of 6-trifluoroacetamido-hexanoic acid (TFA-AHA) to the exposed amino group (TFA-AHA used was a lab stock synthesized previously); and 3) Removal of the trifluoroacetyl protective group. Accordingly, the extension of NTA-tri(GalNAc) with 6-amino-hexanoyl group improved the labeling yield of $^{111}$In-labeled tri(GalNAc), All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

In view of the above, in terms of its general combination and features, the present invention has no been found in the similar products, and has not been disclosed before its filing date. It indeed meets the requirements of a patent and we thus propose this application according to the provisions of the patent law.

What is claimed is:

1. A liver targeting agent comprising a lysine-based nitrilotriacetic acid structure which acquires multivalency by linking carboxyl groups in the nitrilotriacetic acid structure with ahLac (6-aminohexyl-β-lactose), ahGalNAc (6-amino hexyl-β-N-acetylgalactosamine), or GahGalNAc (Glycyl-aminohexyl-acetylgalactosamine).

2. The liver targeting agent according to claim 1, wherein the carboxyl groups in the nitrilotriacetic acid structure link with ahLac (6-aminohexyl-β-lactose).

3. The liver targeting agent according to claim 1, wherein the structure of the lysine-based nitrile triacetic acid is α-dicarboxylmethyl-L-lysine.

4. The liver targeting agent according to claim 2, wherein the agent comprising two molecules of trivalent lactoside linked through the carboxyl groups of an aspartic acid or glutamic acid.

5. The liver targeting agent according to claim 2, wherein the agent is AHA-Asp[DCM-Lys(ahLac)$_3$]$_2$, wherein DCM is dicarboxylmethyl, AHA is aminohexanoyl.

* * * * *